US006882882B2

(12) United States Patent
Struble et al.

(10) Patent No.: US 6,882,882 B2
(45) Date of Patent: Apr. 19, 2005

(54) ATRIOVENTRICULAR DELAY ADJUSTMENT

(75) Inventors: Chester Struble, Eijsden (NL); Lambert Muhlenberg, Landgraaf (NL)

(73) Assignee: Medtronic, Inc., Minneapolis, MN (US)

( * ) Notice: Subject to any disclaimer, the term of this patent is extended or adjusted under 35 U.S.C. 154(b) by 302 days.

(21) Appl. No.: 10/127,038

(22) Filed: Apr. 22, 2002

(65) Prior Publication Data

US 2003/0199936 A1 Oct. 23, 2003

(51) Int. Cl.$^7$ .............................................. A61N 1/365
(52) U.S. Cl. ........................................ 607/9; 600/513
(58) Field of Search ............................... 607/9, 17, 23; 600/509, 513, 526, 528

(56) References Cited

U.S. PATENT DOCUMENTS

| | | | |
|---|---|---|---|
| 4,316,472 A | 2/1982 | Mirowski et al. | |
| 4,375,817 A | 3/1983 | Engle et al. | |
| 4,379,439 A | 4/1983 | Baur | |
| 4,384,585 A | 5/1983 | Zipes | |
| 4,476,868 A | 10/1984 | Thompson | |
| 4,566,063 A | 1/1986 | Zolnowsky et al. | |
| 4,577,633 A | 3/1986 | Berkovits et al. | |
| 4,587,970 A | 5/1986 | Holley et al. | |
| 4,719,921 A | * 1/1988 | Chirife | 607/23 |
| 4,726,380 A | 2/1988 | Vollmann et al. | |
| 4,727,877 A | 3/1988 | Kallok | |
| 4,800,883 A | 1/1989 | Winstrom | |
| 4,821,723 A | 4/1989 | Baker et al. | |
| 4,880,005 A | 11/1989 | Pless et al. | |
| 4,949,719 A | 8/1990 | Pless et al. | |
| 5,024,222 A | 6/1991 | Thacker | |
| 5,099,838 A | 3/1992 | Bardy | |
| 5,131,388 A | 7/1992 | Pless | |
| 5,163,427 A | 11/1992 | Keimel | |
| 5,168,869 A | * 12/1992 | Chirife | 607/25 |
| 5,174,289 A | 12/1992 | Cohen | |
| 5,199,428 A | 4/1993 | Obel et al. | |
| 5,207,218 A | 5/1993 | Carpentier et al. | |
| 5,243,976 A | 9/1993 | Ferek-Petric et al. | |
| 5,269,298 A | 12/1993 | Adams et al. | |
| 5,292,340 A | 3/1994 | Crosby et al. | |
| 5,312,452 A | 5/1994 | Salo | |
| 5,312,453 A | 5/1994 | Shelton et al. | |
| 5,314,430 A | 5/1994 | Bardy | |
| 5,330,507 A | 7/1994 | Schwartz | |
| 5,331,966 A | 7/1994 | Bennett et al. | |

(Continued)

FOREIGN PATENT DOCUMENTS

| | | | |
|---|---|---|---|
| EP | 0 607 951 | 1/2000 | .......... A61N/1/368 |
| EP | 0 596 598 | 11/2000 | .......... A61N/1/368 |
| WO | WO92/8198 | 5/1992 | |
| WO | WO 01/80947 | 11/2001 | .......... A61N/1/368 |

OTHER PUBLICATIONS

"Automatic Tachycardia Recognition" by Arzbaecher et al. PACE May–Jun. 1984, pp. 541–547.

*Primary Examiner*—Kennedy Schaetzle
(74) *Attorney, Agent, or Firm*—Girma Wolde-Michael; Paul H. McDowall

(57) ABSTRACT

In a system that includes a ventricular pacemaker, the system adjusts an atrioventricular delay to synchronize the onset of isovolumetric contraction with the completion of ventricular filling. The system adjusts the atrioventricular delay as a function of electrical and pressure data from the heart. The system further adjusts the atrioventricular delay as a function of measurements of the time interval between a cardiac occurrence such as a ventricular pace and the completion of ventricular filling. The system may also adjust the atrioventricular delay as a function of the heart rate.

71 Claims, 11 Drawing Sheets

U.S. PATENT DOCUMENTS

| | | |
|---|---|---|
| 5,334,222 A | 8/1994 | Salo |
| 5,354,316 A | 10/1994 | Keimel |
| 5,368,040 A | 11/1994 | Carney |
| 5,454,838 A | 10/1995 | Vallana et al. |
| 5,466,245 A | 11/1995 | Spinelli et al. |
| 5,487,752 A | 1/1996 | Salo |
| 5,535,752 A | 7/1996 | Halperin et al. |
| 5,540,727 A | 7/1996 | Tockman et al. |
| 5,545,186 A | 8/1996 | Olson |
| 5,584,868 A | 12/1996 | Salo et al. |
| 5,626,623 A | 5/1997 | Kieval et al. |
| 5,643,327 A | 7/1997 | Dawson et al. |
| 5,800,471 A | 9/1998 | Baumann |
| 5,810,735 A | 9/1998 | Halperin et al. |
| 5,836,987 A | 11/1998 | Baumann et al. |
| 6,144,880 A | 11/2000 | Ding et al. |
| 6,208,901 B1 | 3/2001 | Hartung |
| 6,280,389 B1 | 8/2001 | Ding et al. |
| 6,792,308 B1 * | 9/2004 | Corbucci ............... 607/17 |

* cited by examiner

ATRIOVENTRICULAR DELAY ADJUSTMENT

FIELD OF THE INVENTION

The present invention relates to cardiac pacemakers, and particularly to cardiac pacemakers that pace one or more ventricles of the heart.

BACKGROUND

Atrioventricular synchronized dual chamber pacing modes, such as the multi-programmable VDD, VDDR, DDD and DDDR pacing modes, have been widely adopted in implantable pacemakers for providing atrioventricular synchronized pacing. A pacemaker operating in such a pacing mode may include an atrial sense amplifier that detects atrial depolarizations and generates an atrial sense event signal in response to an atrial depolarization. In some pacemakers, the same electrode that senses atrial events can also deliver an atrial pacing pulse when the atrium fails to activate spontaneously.

Following the atrial event, whether sensed or paced, and following the expiration of an atrioventricular delay, the pacemaker supplies a ventricular pacing pulse to one or more ventricles. In some pacemakers, delivery of the ventricular pacing pulse is inhibited when the ventricles activate spontaneously. Some DDD and DDDR mode pacers employ separate atrioventricular delays for sensed and paced atrial events.

The atrioventricular delay is important to atrioventricular synchrony and hemodynamic performance. In general, atrioventricular synchronous pacemakers have the capability of tracking the patients natural sinus rhythm and preserving the hemodynamic contribution of the atrial contraction over a wide range of heart rates. The importance of atrioventricular mechanical synchrony is described in greater detail in commonly assigned U.S. Pat. No. 5,626,623, incorporated herein by reference in its entirety.

In prior art pacemakers, the atrioventricular delay need not be a fixed interval, but can be lengthened or shortened in response to various factors. Some prior art devices, for example, use pressure data obtained from the right and/or left ventricles of the heart to adjust the atrioventricular delay. In particular, prior art devices have adjusted the atrioventricular delay as a function of the estimated pulmonary artery diastolic (ePAD) pressure measured in the right ventricle, or as a function of heart contractility, or as a function of measured cardiac output. Other prior art devices have adjusted the atrioventricular delay and observed the resulting effects on ventricular pressures. Examples of these techniques and/or devices may be found in the issued U.S. Patents listed in Table 1 below.

TABLE 1

| U.S. Pat. No. | Inventor | Issue Date |
| --- | --- | --- |
| 5,024,222 | Thacker | Jun. 18, 1991 |
| 5,292,340 | Crosby et al. | May 8, 1994 |
| 5,312,452 | Salo | May 17, 1994 |
| 5,334,222 | Salo et al. | Aug. 2, 1994 |
| 5,368,040 | Carney | Nov. 29, 1994 |
| 5,454,838 | Vallana et al. | Oct. 3, 1995 |
| 5,466,245 | Spinelli et al. | Nov. 14, 1995 |
| 5,487,752 | Salo et al. | Jan. 30, 1996 |
| 5,535,752 | Halperin et al. | Jul. 16, 1996 |

TABLE 1-continued

| U.S. Pat. No. | Inventor | Issue Date |
| --- | --- | --- |
| 5,540,727 | Tockman et al. | Jul. 30, 1996 |
| 5,584,868 | Salo et al. | Dec. 17, 1996 |
| 5,626,623 | Kieval et al. | May 6, 1997 |
| 5,643,327 | Dawson et al. | Jul. 1, 1997 |
| 5,800,471 | Baumann | Sep. 1, 1998 |
| 5,810,735 | Halperin et al. | Sep. 22, 1998 |
| 5,836,987 | Baumann et al. | Nov. 17, 1998 |
| 6,144,880 | Ding et al. | Nov. 7, 2000 |
| 6,280,389 B1 | Ding et al. | Aug. 28, 2001 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to adjusting the atrioventricular delay in response to sensed factors. These problems include, for example, an inability to adjust the atrioventricular delay to cause ventricular isovolumetric contraction to coincide with the end of ventricular filling.

One object of the present invention is promotion of hemodynamic performance by selecting an atrioventricular delay that promotes mechanical atrioventricular synchrony. In particular, it is an object of the present invention to cause ventricular isovolumetric contraction to occur immediately upon completion of filling of the ventricles. When ventricular isovolumetric contraction commences before the ventricles are filled, or if there is a delay between completion of filling and isovolumetric contraction, the cardiac output may be reduced. When isovolumetric contraction follows filling promptly, the cardiac output of the patient is improved, and the hemodynamic performance of the heart is near optimum.

One advantage of the invention, therefore, is that the invention improves hemodynamic performance. The invention improves hemodynamic performance by adjusting the atrioventricular delay so that ventricular isovolumetric contraction occurs promptly once filling of the ventricles is completed.

Another object of the invention is to use indicators that directly reflect quantities of interest. In particular, the onset of isovolumetric contraction is reflected in a sharp upturn in the ventricular pressure. This upturn can be detected by monitoring the pressure curve and/or the derivative of the pressure curve. The closure of the atrioventricular valve is reflected by the blood flow through the valve, i.e., when the blood flow through the valve ceases, the valve is closed. The invention advantageously considers direct indicators, rather than derived indicators, of the mechanics to be synchronized.

A further object of the invention is to provide an atrioventricular delay that is adjustable in response to a change in heart rate, so that enhanced hemodynamic performance may be maintained when the heart rate changes. In one embodiment of the invention, measurements may be taken of the interval between a ventricular pace and mitral valve closure at two or more heart rates. The implantable device may adjust the atrioventricular delay to account for different filling times at different heart rates.

The invention is therefore advantageous in that the invention adapts to changing conditions. In particular, the invention advantageously maintains hemodynamic performance under changing conditions and does so automatically.

In general, the present invention includes features that address the deficiencies in the prior art and that realize the objectives and advantages. In particular, the invention may include sensors to collect pressure data, such as pressure data from the left ventricle. The pressure data may be used to measure the time interval between a cardiac occurrence, such as a ventricular pace, and the onset of ventricular isovolumetric contraction. The invention may also include memory that stores measurements of one or more time intervals between the cardiac occurrence and the completion of ventricular filling. Further, the invention may include a processor that selects an atrioventricular delay to synchronize the onset of isovolumetric contraction with the completion of ventricular filling. The processor may further adjust the atrioventricular delay as a function of the heart rate of the patient.

Various embodiments of the present invention have the object of solving at least one of the foregoing problems.

DETAILED DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
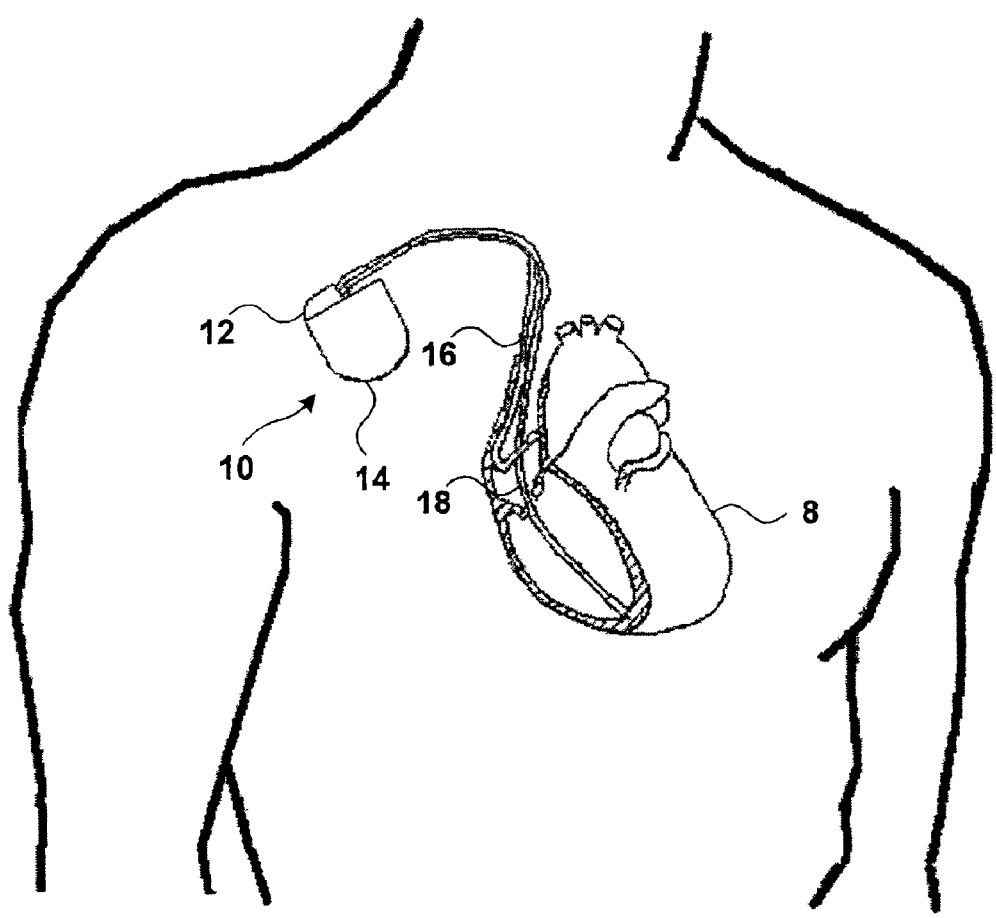
FIG. 1 is a schematic view of an implantable medical device in the chest of a patient.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to connector module 12 of hermetically sealed enclosure 14 and implanted near human or mammalian heart 8. Pacing and sensing leads 16 and 18 sense electrical signals attendant to the depolarization and repolarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al., or U.S. Pat. No. 5,144,949 to Olson, all hereby incorporated by reference herein, each in its respective entirety.

Figure 2:
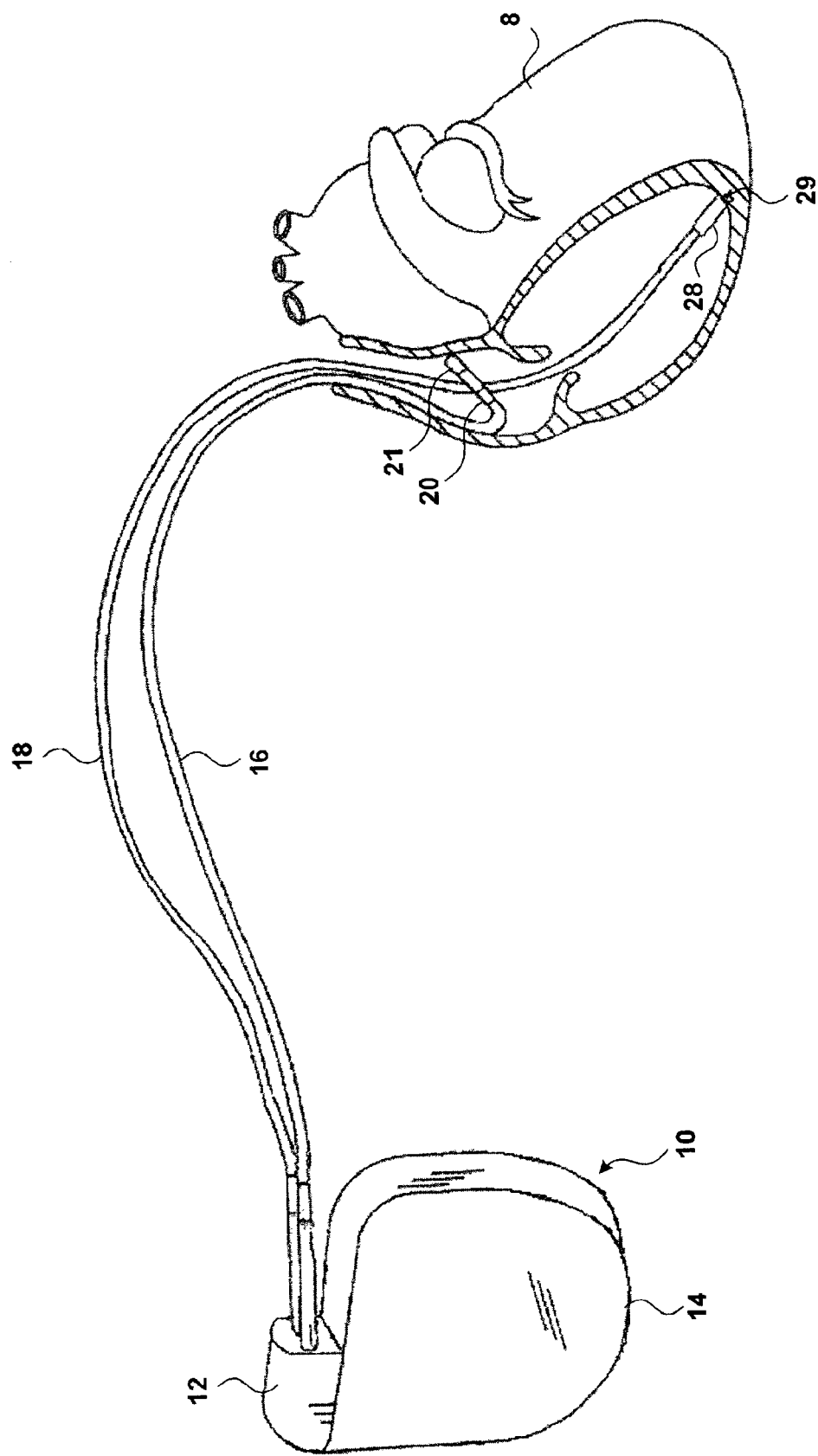
FIG. 2 shows the implantable medical device of FIG. 1 located in and near a heart.

FIG. 2 shows connector module 12 and hermetically sealed enclosure 14 of IMD 10 located in and near human or mammalian heart 8. Atrial and ventricular pacing leads 16 and 18 extend from connector module 12 to the right atrium and ventricle, respectively, of heart 8. Atrial electrodes 20 and 21 disposed at the distal end of atrial pacing lead 16 are located in the right atrium. Ventricular electrodes 28 and 29 disposed at the distal end of ventricular pacing lead 18 are located in the right ventricle.

Leads 16 and 18 may sense the activity of the right atrium or right ventricle and may also deliver a stimulus. Leads 16 and 18 may also deliver a stimulus to the right atrium or right ventricle. In some patients, stimulation of the right ventricle of heart 8 takes place after IMD 10 senses an atrial activation via lead 16, or after IMD 10 delivers a pacing pulse to the right atrium via lead 16. The time interval between the atrial sense or pace and the ventricular stimulation is called the atrioventricular delay. As will be described in more detail below, IMD 10 may adjust the atrioventricular delay to improve the hemodynamic efficiency of heart 8.

Figure 3:
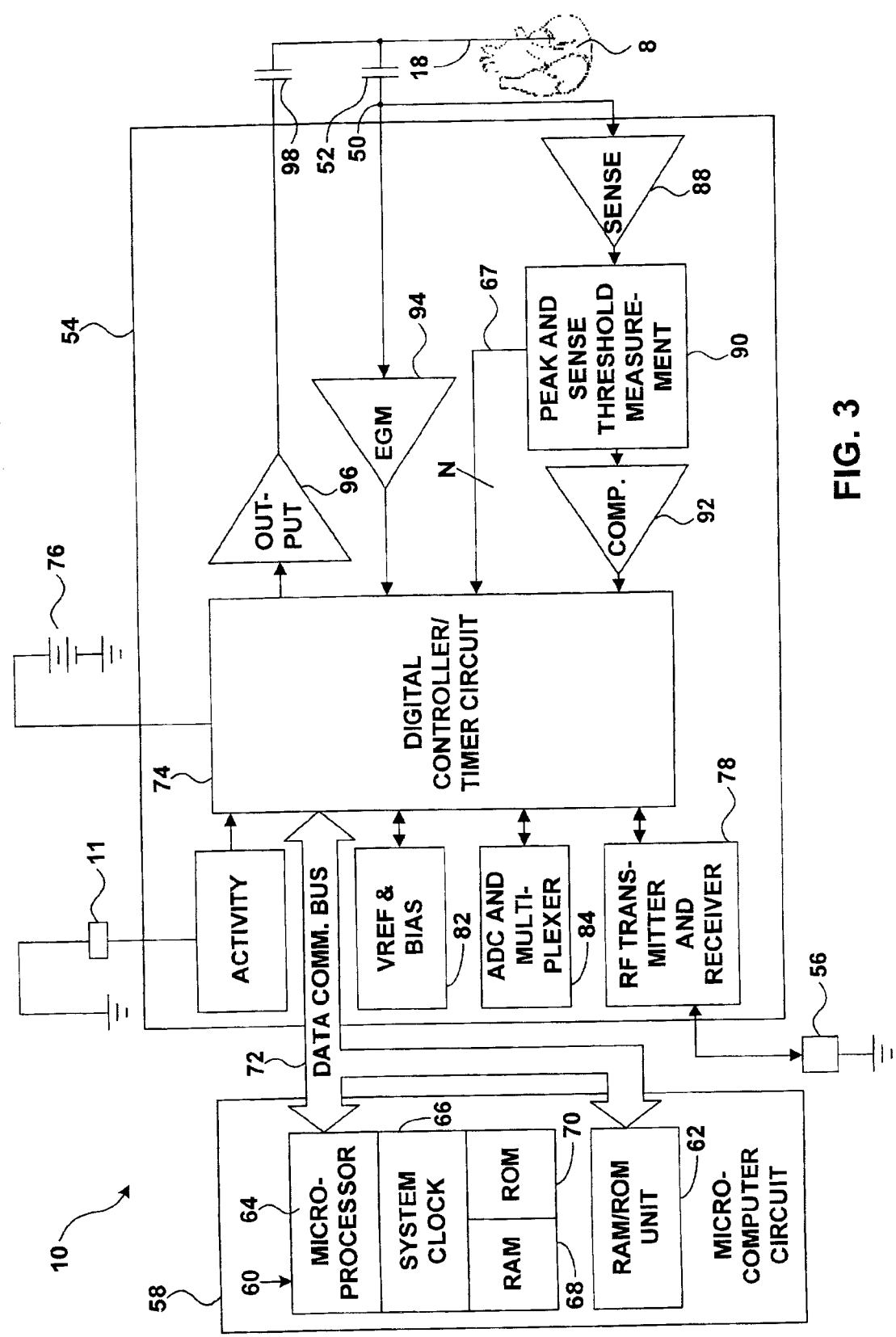
FIG. 3 is a block diagram illustrating the constituent components of an implantable medical device.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which is preferably a piezoceramic accelerometer bonded to a hybrid circuit located inside enclosure 14 (shown in FIGS. 1 and 2). Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto. However, it is understood that similar circuitry and connections not explicitly shown in FIG. 3 apply to lead 16 (shown in FIGS. 1 and 2).

IMD 10 in FIG. 3 is most preferably programmable by means of an external programming unit (not shown in the figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker. As will be described below, data may be provided to IMD 10 via telemetry that IMD 10 may use to adjust the atrioventricular delay.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing with heart 8, activity sensor 11, antenna 56 and circuits for the application of stimulating pulses to heart 8. The rate of heart 8 is controlled by software-implemented algorithms stored within microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures.

Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled from microprocessor 64 via data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is also provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides amplified pacing stimuli to patient's heart 8 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with one or more leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, and U.S. Pat. No. 4,821,723 to Baker et al., all hereby incorporated by reference herein, each in its respective entirety.

Figure 4:
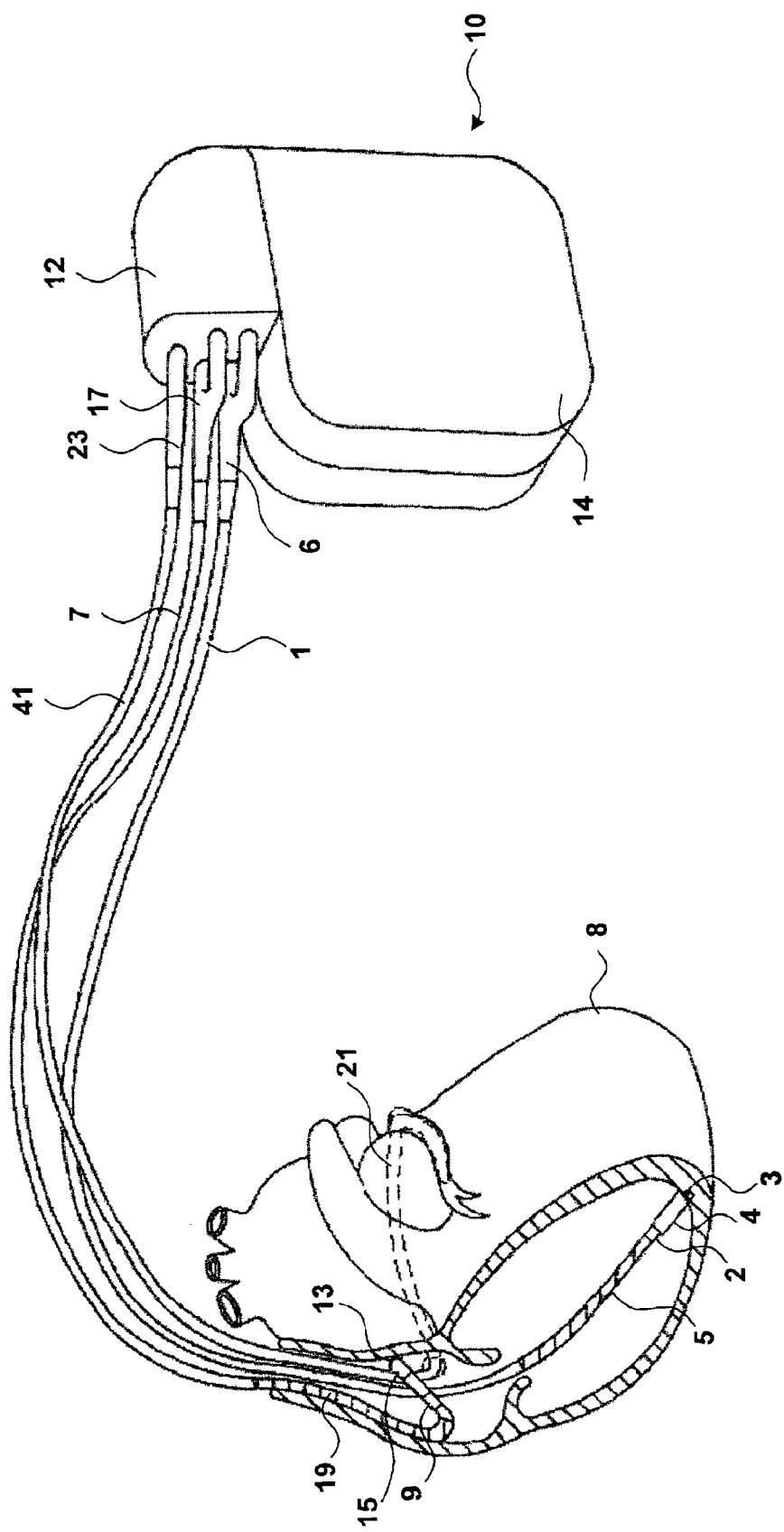
FIG. 4 shows another implantable medical device, a pacemaker-cardioverter-defibrillator, located in and near a heart.
Figure 5:
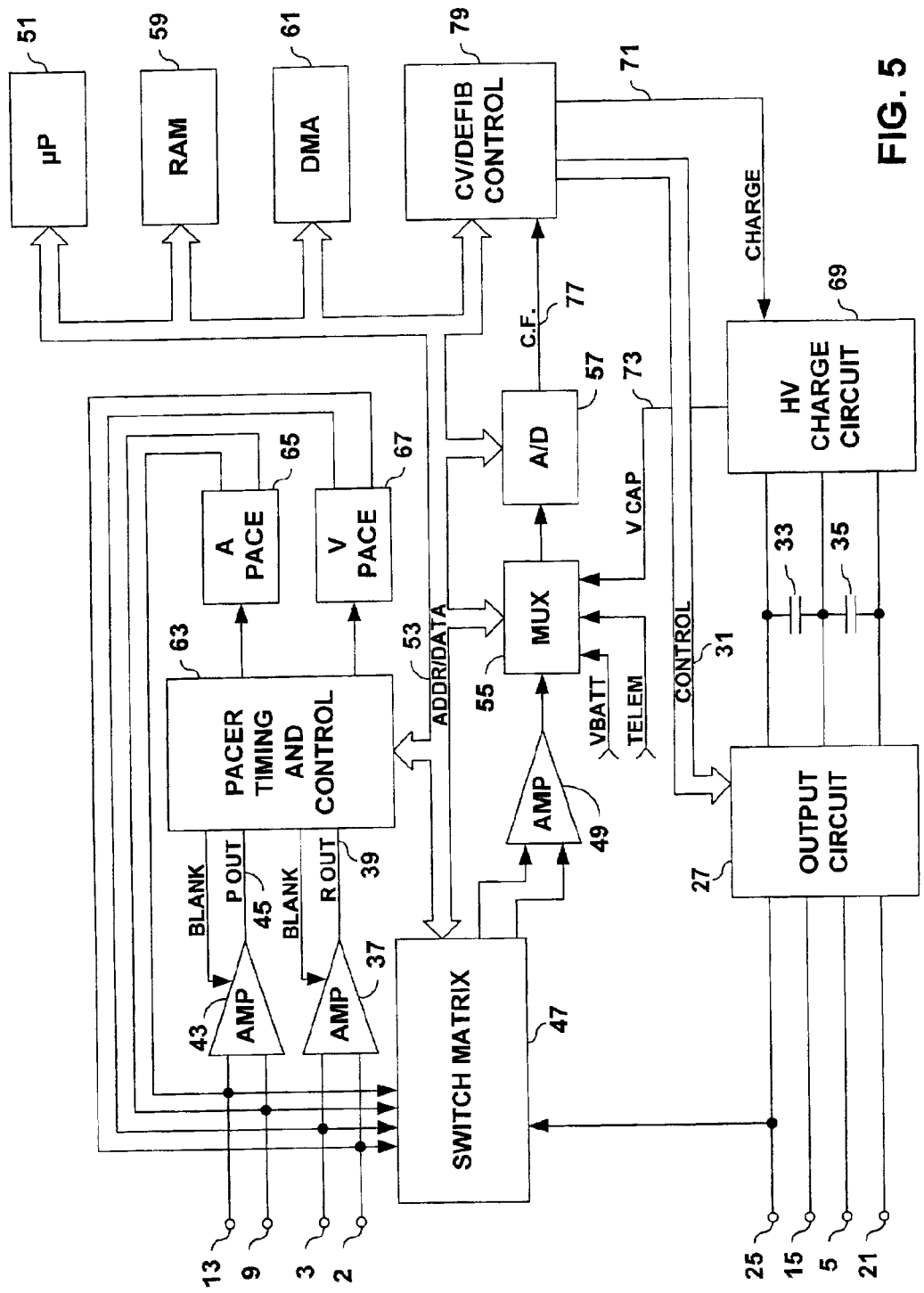
FIG. 5 is a functional schematic diagram of one embodiment of an implantable medical device.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Elongated coil electrode 5, which is a defibrillation electrode 5, may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

In some modes, IMD 10 may pace the right ventricle with electrodes 2 and 3 following atrial activity sensed or paced via electrodes 13 and 9 and following an atrioventricular delay. As will be described in more detail below, IMD 10 may adjust the atrioventricular delay to improve the hemodynamic efficiency of heart 8.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. Elongated coil defibrillation electrode 41 may be about 5 cm in length.

IMD 10 is shown in FIG. 4 in combination with leads 1, 7 and 41, and lead connector assemblies 23, 17 and 6 inserted into connector module 12. Optionally, insulation of the outward facing portion of housing 14 of IMD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of IMD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of IMD 10. Electrodes 25, 15, 21 and 5 are coupled to high voltage output circuit 27, which includes high voltage switches controlled by CV/defib control logic 79 via control bus 31. Switches disposed within circuit 27 determine which electrodes are employed and which electrodes are coupled to the positive and negative terminals of a capacitor bank (which includes capacitors 33 and 35) during delivery of defibrillation pulses.

Electrodes 2 and 3 are located on or in the ventricle of the patient and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium of the patient and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824 to Keimel et al., hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art. In addition, circuitry 63 may control the atrioventricular delay that separates a sensed or paced atrial event from a paced ventricular event.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R—R intervals, P—P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The rate of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al., and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/8198, by Adams et al., and in the article "Automatic Tachycardia Recognition," by Arzbaecher et al., published in PACE, May-June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al., and U.S. Pat. No. 4,587,970, issued to Holley et al., all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 79, which initiates charging of high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al., and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 79 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above-cited patent issued to Mehra and in U.S. Pat. No. 4,727,877 to Kallok, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
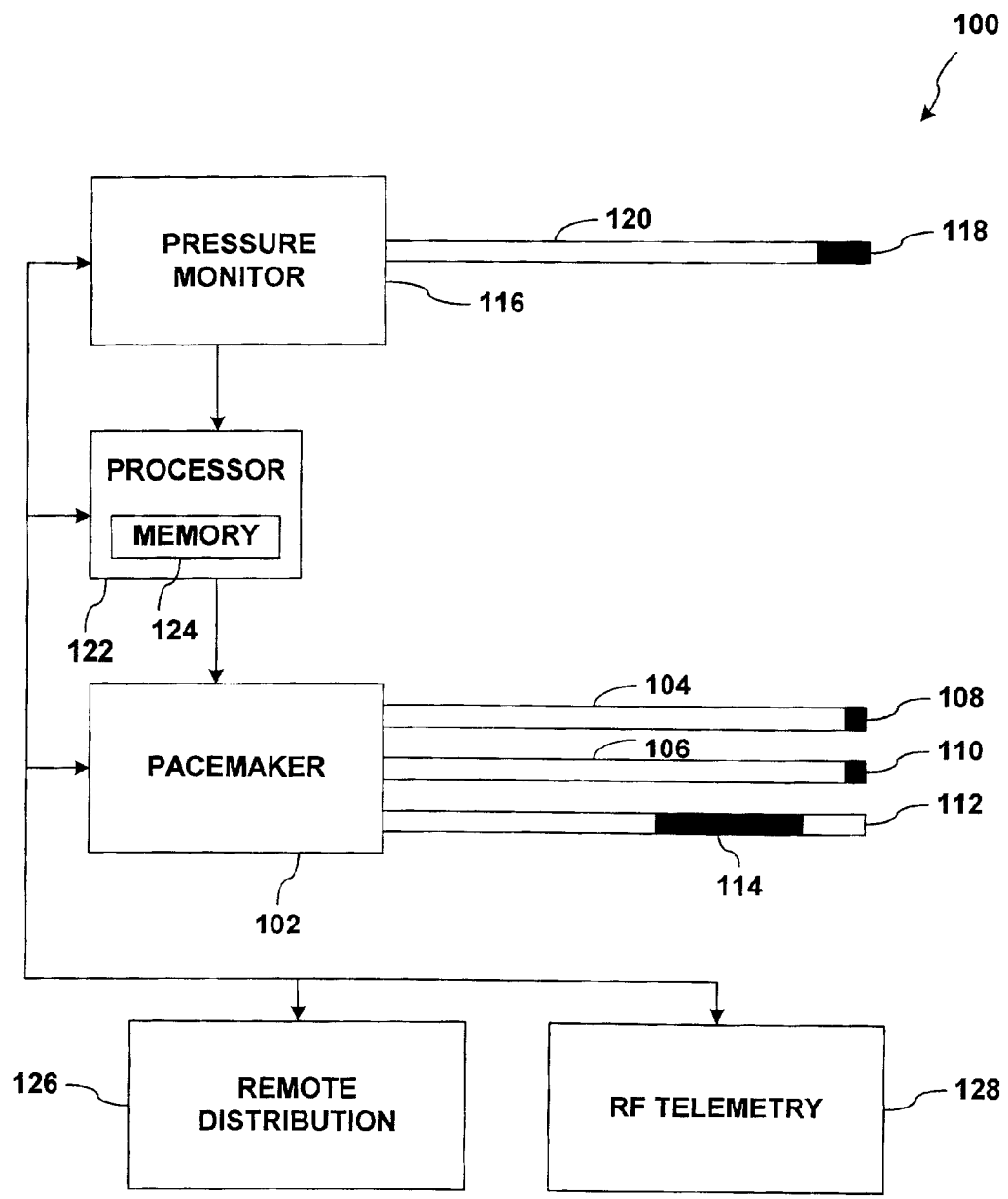
FIG. 6 is a diagram of a system including a pressure monitor and a cardiac pacemaker.

FIG. 6 shows a system 100 illustrating an embodiment of the invention, in which pressure measurements are used to adjust the atrioventricular delay. System 100, which may be implantable in a human being or a mammal, includes cardiac pacemaker 102. Pacemaker 102 may pace one or more chambers of heart 8 (not shown in FIG. 6) using one or more pacing modes. Pacemaker 102 may be, for example, a device that senses and paces the right side of heart 8 such as is shown in FIG. 2, or a pacemaker-cardioverter-defibrillator that senses and paces the right and left sides of heart 8 as shown in FIG. 4. The invention is not limited to the exemplary pacemakers shown in FIGS. 2 and 4, however.

Pacemaker 102 may be one of the many forms of implantable medical devices 10 described above, or may be an external pacemaker. Atrial electrode 108 may correspond to any of electrodes 9, 13, 20 or 21 described above, ventricular electrode 110 may correspond to any of electrodes 2, 3, 28 and 29 described above, and defibrillation coil electrode 114 may correspond to elongated coil electrode 5 described above. The invention is not limited to the exemplary devices and systems shown in FIGS. 1 through 5, however.

System 100 may monitor the heart rate of the patient continuously by observing signals sensed via electrodes 108 and 110 and/or by monitoring paces delivered via electrodes 108 and 110. Pacemaker 102 may further be coupled to lead 112, which includes defibrillation coil electrode 114. Alternatively, defibrillation coil electrode 114 may be coupled to lead 104 or 106. FIG. 4, for example, shows defibrillation coil 5 coupled to ventricular lead 1.

The invention includes techniques for controlling the timing of pacing pulses as a function of the pressure of the blood inside the patient's heart 8. System 100 includes pressure monitor 116, which is coupled to a pressure sensor 118 by a lead 120. Pressure sensor 118 responds to the absolute pressure inside heart 8, and may be, for example, a capacitive or piezoelectric absolute pressure sensor. Sensor 118 may generate pressure signals itself or may modulate pressure signals conducted through lead 120. The pressure signals are a function of the fluid pressure at the site where pressure sensor 118 is disposed. In one embodiment of the invention, pressure sensor 118 is disposed in the left ventricle of heart 8. Pressure monitor 116 receives, monitors and analyzes the pressure signals, as will be described in more detail below. An example of pressure monitor 116 is the Chronicle™ Implantable Hemodynamic Monitor manufactured by and commercially available from Medtronic, Inc. of Minneapolis, Minn.

Pacemaker 102 and pressure monitor 116 are coupled to processor 122. Processor 122 is associated with memory 124. Processor 122 is shown as logically separate from pacemaker 102 and pressure monitor 116, but in practice processor 122 may be housed inside pressure monitor 116, or inside pacemaker 102. Processor 122 may be included in microprocessor 51 and/or pacer timing/control circuitry 63 in the embodiment of implanted medical device 10 shown in FIG. 5, for example. Alternatively, processor 122 may be separate from both pressure monitor 116 and pacemaker 102. Further, pressure monitor 116, pacemaker 102 and processor 122 may be realized as a single implantable device.

Data collected by pacemaker 102, pressure monitor 116 and/or processor 122 may be retrieved via input/output devices such as remote distribution link 126 or RF telemetry 128. Further, pacemaker 102, pressure monitor 116 and/or processor 122 may receive information such as data or programming instructions via input/output devices 126, 128. Remote distribution link 126 may provide a channel for uploading or downloading information over a telephone line or over the internet, for example. RF telemetry 128 may communicate information on a dedicated channel. Typically, a patient is required to visit an office of a physician when information is to be uploaded or downloaded via RF telemetry 128.

Figure 7:
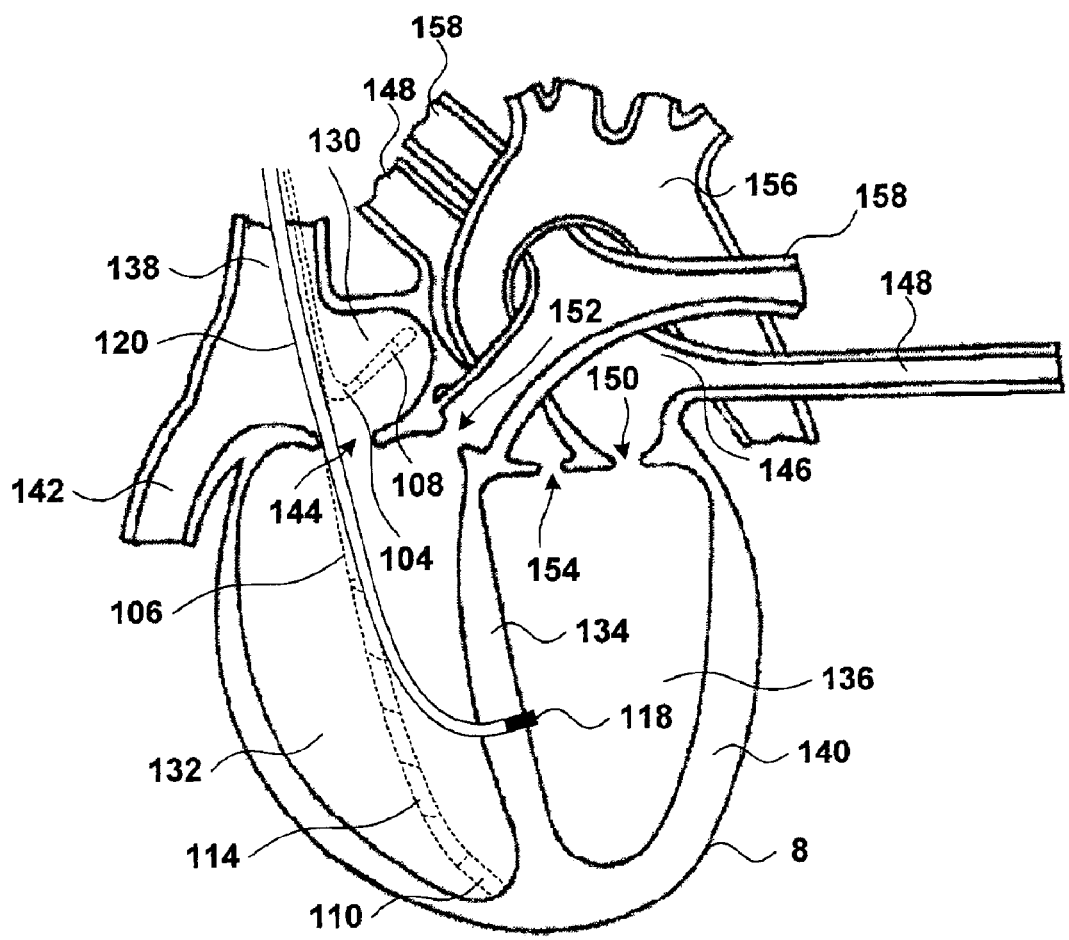
FIG. 7 is a diagram of a human heart, with pacing and sensing electrodes in the right atrium and right ventricle, and a pressure sensor disposed in the left ventricle.

FIG. 7 is a diagram of human heart 8 showing an exemplary application of the invention. Atrial electrode 108 is disposed in right atrium 130. Ventricular lead 110 is disposed in right ventricle 132. Lead 120 descends into right ventricle 132 and penetrates the interventricular septum 134. Pressure sensor 118 is therefore disposed in left ventricle 136 and is responsive to the pressure inside left ventricle 136. Leads 104, 106 and 120 extend from right atrium 130 through the superior vena cava 138. Leads 104, 106 and 120 further extend through the circulatory system, eventually exiting the circulatory system and coupling to implanted pressure monitor 116 or pacemaker 102 (not shown in FIG. 7).

The position of leads, sensors and electrodes shown in FIG. 7 is for purposes of illustration, and the invention is not limited to the application shown. For example, ventricular electrode 110 and pressure sensor 118 may be included on a single lead. Pressure sensor 118 may be disposed in left ventricle 136 through septum 134 as shown, but ventricular electrode 110 would be disposed in right ventricle 132 proximate to septum 134. In another variation, pressure lead 120 does not descend through right atrium 130 or right ventricle 132, but is disposed outside heart 8 and penetrates the left ventricular wall 140, thereby disposing pressure sensor 118 in left ventricle.

Furthermore, the invention is not limited to applications in which electrodes are disposed in right atrium 130 and right ventricle 132, but may be applied in any number of applications such as applications disposing sensing and/or pacing electrodes in three or four chambers of heart 8. Moreover, the invention may be practiced with pressure sensor 118 disposed in right ventricle 132, although pressures in left ventricle 136 are generally more useful. The invention encompasses all of these variations.

During a cardiac cycle, heart 8 relaxes to fill and contracts to empty. During atrial and ventricular diastole, passive filling takes place. During passive filling, oxygen-poor blood enters right atrium 130 via the superior vena cava 138 and the inferior vena cava 142. Oxygen-poor blood also enters right ventricle 132 through the tricuspid or right atrioventricular valve 144. At the same time, oxygen-rich blood enters the left atrium 146 via the pulmonary veins 148, and also enters left ventricle 136 through the mitral or left atrioventricular valve 150.

Atrial depolarization causes atria 130, 146 to contract, forcing blood from atria 130, 146 into ventricles 132, 136. Ventricular filling due to atrial contraction is called "active filling." Throughout active filling, tricuspid valve 144 and mitral valve 150 remain open. When active filling is completed, tricuspid valve 144 and mitral valve 150 close.

Ventricular systole begins with the contraction of ventricles 132, 136. As contraction begins, tricuspid valve 144 and mitral valve 150 are closed, as are the pulmonary valve 152 and aortic valve 154. Because valves 144, 150, 152, 154 are closed, no blood can enter or leave ventricles 132, 136, and the contraction is isovolumetric.

In left ventricle 136, aortic valve 154 remains closed until the pressure in left ventricle 136 exceeds the pressure in the aorta 156. At this point, aortic valve 154 is forced open and blood is ejected into aorta 156. Similarly, pulmonary valve 152 remains closed until the pressure in right ventricle 132 exceeds the pressure in the pulmonary arteries 158, at which time pulmonary valve 152 is forced open and blood is ejected into pulmonary arteries 158. As ventricles 132, 136 relax, pulmonary valve 152 and aortic valve 154 close and ventricles 132, 136 undergo a period of isovolumetric relaxation. When the pressure in ventricles 132, 136 falls below the pressure in the atria 130, 146, then atrioventricular valves 144, 150 open and passive filling begins anew.

In a pacemaker-assisted heart, the timing of atrial and/or ventricular contractions may be controlled by pacemaker 102. In one patient, for example, pacemaker 102 may sense an intrinsic atrial activation via electrode 108, and may deliver a ventricular pacing pulse via electrode 110 following an atrioventricular delay. In another patient, pacemaker 102 may deliver an atrial pacing pulse via electrode 108, and a ventricular pacing pulse via electrode 110 following an atrioventricular delay. The atrioventricular delay is a parameter that is applied by pacemaker 102 to deliver pacing. The invention is generally directed to techniques for changing the atrioventricular delay parameter in response to paces and/or measurements made by pacemaker 102 and/or measurements made by pressure monitor 116. In particular, the invention is directed to techniques for changing the atrioventricular delay parameter to synchronize the onset of ventricular isovolumetric contraction with the completion of ventricular filling, thereby improving the hemodynamic efficiency of heart 8.

When pacemaker 102 delivers a pacing pulse to a ventricle such as right ventricle 132, there is an electrical activation of right ventricle 132. Right ventricle 132 does not start ventricular contraction immediately upon electrical activation, however. There is a time interval, called the "electromechanical delay," between the electrical activation and the start of isovolumetric contraction.

Ideally, isovolumetric contraction should begin immediately upon completion of active filling, which follows the passive filling phase. If isovolumetric contraction begins before filling is completed, the ventricle begins contraction before the ventricle is full. Truncation of active filling results, thereby reducing the stroke volume of the heart. If isovolumetric contraction begins too long after filling is completed, the ventricle waits for contraction to begin. While the ventricle waits, blood may seep back into the atrium through the atrioventricular valve. Seepage results in backward fluid flow and a reduction of blood in the ventricle, resulting in a loss of stroke volume. Consequently, the heart operates most efficiently when isovolumetric contraction begins promptly upon completion of active filling. When isovolumetric contraction begins earlier or later, the hemodynamic efficiency of the heart is reduced.

By adjusting the atrioventricular delay, a pacing pulse delivered by pacemaker 102 may be timed to bring about isovolumetric contraction promptly upon completion of active filling. In this way, the invention enhances the hemodynamic efficiency of the heart and avoids reduction of cardiac output due to early or late contraction, as described above.

Figure 8:
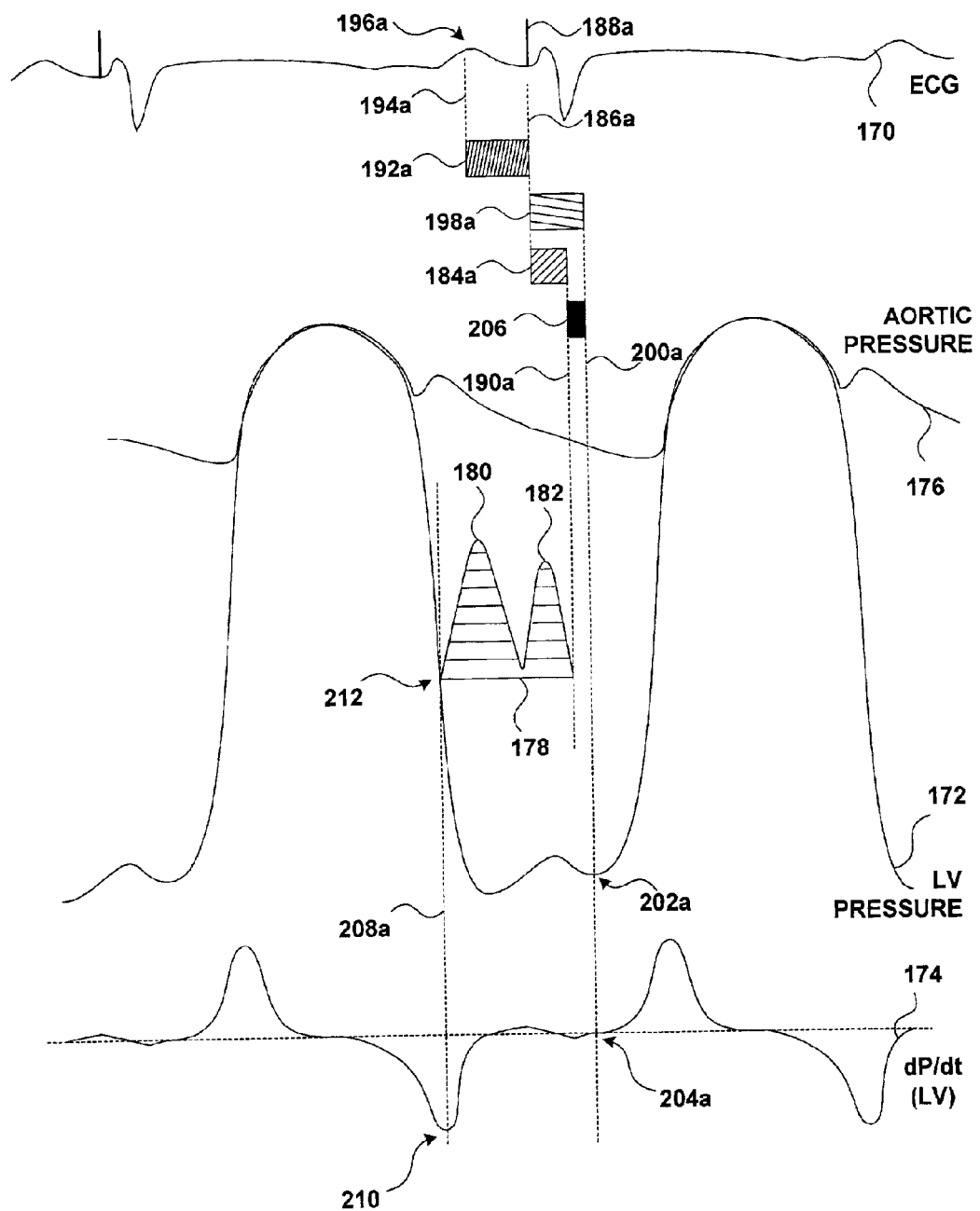
FIG. 8 is a timing diagram illustrating an undesirable atrioventricular delay, including an electrocardiogram signal, a corresponding left ventricular pressure signal, a derivative of the left ventricular pressure signal, and a mitral valve flow pattern.

FIG. 8 is a timing diagram showing an electrocardiogram (ECG) signal 170 and a corresponding left ventricular pressure 172. ECG 170 may be sensed by, for example, an electrode on an external electrocardiograph. Left ventricular pressure 172 may be sensed via pressure sensor 118 disposed in left ventricle 136, such as is shown in FIG. 7. FIG. 8 also shows the derivative 174 of the left ventricular pressure 172 with respect to time, denoted dP/dt. Derivative dP/dt 174 may be computed by pressure monitor 116 or processor 122. FIG. 8 further shows the aortic pressure 176, which is shown for reference purposes but is not directly measured via any instruments described herein.

FIG. 8 further shows a flow pattern 178, representing the flow of blood into left ventricle 136 through mitral valve 150. Flow pattern 178 demonstrates two distinctive waves. An E-wave 180 represents the blood flow into left ventricle 136 during passive filling, and an A-wave 182 represents the blood flow into left ventricle 136 during active filling. Flow pattern 178 may be sensed using techniques such as echo-Doppler sensing.

In general, echo-Doppler sensing techniques involve the use of ultrasound to observe the interior of heart 8 and locate mitral valve 150. Once mitral valve 150 is located, blood flow through mitral valve 150 can be observed. In particular, pulsed-wave echo-Doppler techniques can be employed to observe the onset of blood flow, the speed and direction of the flow, the diameter of the valve, and the time flow stops. Important to the invention is the time that flow stops, because flow stoppage indicates the closing of mitral valve 150.

The flow pattern may be measured with respect to another signal, such as ECG signal 170. ECG may be sensed independently of electrodes 108 and 110. In other words, a flow pattern sensor such as an echo-Doppler sensor may include a dedicated electrode to sense ECG signal 170. A flow pattern sensor such as an echo-Doppler sensor may therefore measure a time interval 184a between the time 186a a pacing pulse 188a is administered and the time of mitral valve closure 190a. This interval 184a, which represents the time between a ventricular pace 186a and mitral valve closure 190a, may be denoted PACE_CLOSURE_INTERVAL 184a.

Measurements of PACE_CLOSURE_INTERVAL 184a may involve an office visit by the patient. Due to practical considerations, such as practical problems with placing a flow pattern sensor proximate to mitral valve 150, it may be undesirable to implant the flow pattern sensor in the patient. Instead, it may be more practical for medical personnel to operate the flow pattern sensor from outside the body of the patient. As will be described below, several measurements of PACE_CLOSURE_INTERVAL 184a may be made during a single office visit. In particular, PACE_CLOSURE_INTERVAL 184a may vary as a function of heart rate, and PACE_CLOSURE_INTERVAL 184a may be measured at several different heart rates.

Because PACE_CLOSURE_INTERVAL 184a may vary as a function of heart rate, implantable system 100 may be programmed to select a value of PACE_CLOSURE_INTERVAL 184a as a function of heart rate. In particular, system 100 may measure the heart rate of the patient and select a value for PACE_CLOSURE_INTERVAL 184a that corresponds to the measured heart rate. Techniques for relating PACE_CLOSURE_INTERVAL 184a to heart rate will be described in more detail below.

While PACE_CLOSURE_INTERVAL 184a is being measured, the patient receives ventricular paces. These ventricular paces may be detected by, for example, an electrocardiograph attached to the patient. Furthermore, the ventricular paces follow a sensed or atrial event by a known atrioventricular delay. This "baseline" atrioventricular delay is programmed into pacemaker 102. A typical baseline atrioventricular delay may be, for example, 150 ms after a sensed atrial event. The same baseline atrioventricular delay may be used for all measurements of PACE_CLOSURE_INTERVAL 184a at all heart rates.

FIG. 8 shows the baseline atrioventricular delay 192a. Baseline atrioventricular delay 192a represents the interval between the time 194a of a sensed atrial event 196a and the time 186a of a ventricular pacing pulse 188a. Baseline atrioventricular delay 192a is regulated by system 100. In particular, system 100 may apply an atrioventricular delay that is shorter or longer than baseline atrioventricular delay 192a.

As shown in FIG. 8, the atrial event is a sensed P-wave 196a. Baseline atrioventricular delay 192a may also represent the time interval between an atrial pace (not shown) and a ventricular pace. Baseline atrioventricular delay 192a may be of one duration when an atrial event is sensed, and may be of a different duration when an atrial event is paced.

Typically, an atrioventricular delay following a paced atrial event is about 30 ms longer than an atrioventricular delay following a sensed atrial event. The invention may be applied to atrioventricular delays that follow paced atrial events as well as to atrioventricular delays that follow sensed atrial events.

Implanted system 100 may measure a time interval 198a that may be denoted PACE_CONTRACTION_INTERVAL. PACE_CONTRACTION_INTERVAL 198a represents the interval between the time 186a of a ventricular pace 188a and the onset of isovolumetric contraction 200a. On left ventricular pressure curve 172, the beginning of isovolumetric contraction is indicated by a sharp upturn 202a in the curve. This sharp upturn may be sensed by reference to dP/dt curve 174, and detecting zero-crossing 204a.

When implanted system 100 measures PACE_CONTRACTION_INTERVAL 198a and when system 100 obtains a value of PACE_CLOSURE_INTERVAL 184a, system 100 can calculate DELTA 206. DELTA 206 is the time difference between PACE_CONTRACTION_INTERVAL 198a and PACE_CLOSURE_INTERVAL 184a. When PACE_CLOSURE_INTERVAL 184a is subtracted from PACE_CONTRACTION_INTERVAL 198a, DELTA 206 should be positive. When DELTA 206 is positive, as it is in FIG. 8, left ventricle 136 waits for a short time interval for contraction to begin. This waiting interval is equal to the positive DELTA 206. During this interval, blood under pressure may seep out from left ventricle 136 into left atrium 146 through mitral valve 150. By shortening atrioventricular delay 192a, DELTA 206 can be driven to zero, thereby causing isovolumetric contraction to commence promptly upon completion of active filling and consequently enhancing the hemodynamic efficiency of heart 8.

Baseline atrioventricular delay 192a is chosen so that DELTA 206 will not normally be negative. When the baseline atrioventricular delay is too short, left ventricle 136 begins isovolumetric contraction before filling is completed, resulting in a truncation of A-wave 182 and a reduced cardiac output. The short baseline atrioventricular delay will be noticed when data are collected using a flow pattern sensor such as an echo-Doppler sensor. In particular, A-wave 182 will not appear to have naturally terminated, but will appear to have been truncated because of premature closure of mitral valve 150. Selection of a fairly long baseline atrioventricular delay, such as 150 ms, will in many cases prevent truncation of A-wave 182.

Implanted system 100 computes DELTA 206 as a function of measurements made by a flow pattern sensor such as echo-Doppler. Implanted system 100 may detect the time 208a of opening of mitral valve 150 by reference to dP/dt curve 174. When mitral valve 150 opens, dP/dt is at a minimum 210. This peak may be called the peak negative dp/dt or –dP/dt max. In other words, opening of mitral valve 150 begins the process of passive filling, which results in an inflection point 212 in left ventricular pressure curve 172. Implanted system 100 ordinarily may be unable to accurately detect, however, the time of closure of mitral valve 150, and may therefore be unable to measure PACE_CLOSURE_INTERVAL 184a accurately.

Figure 9:
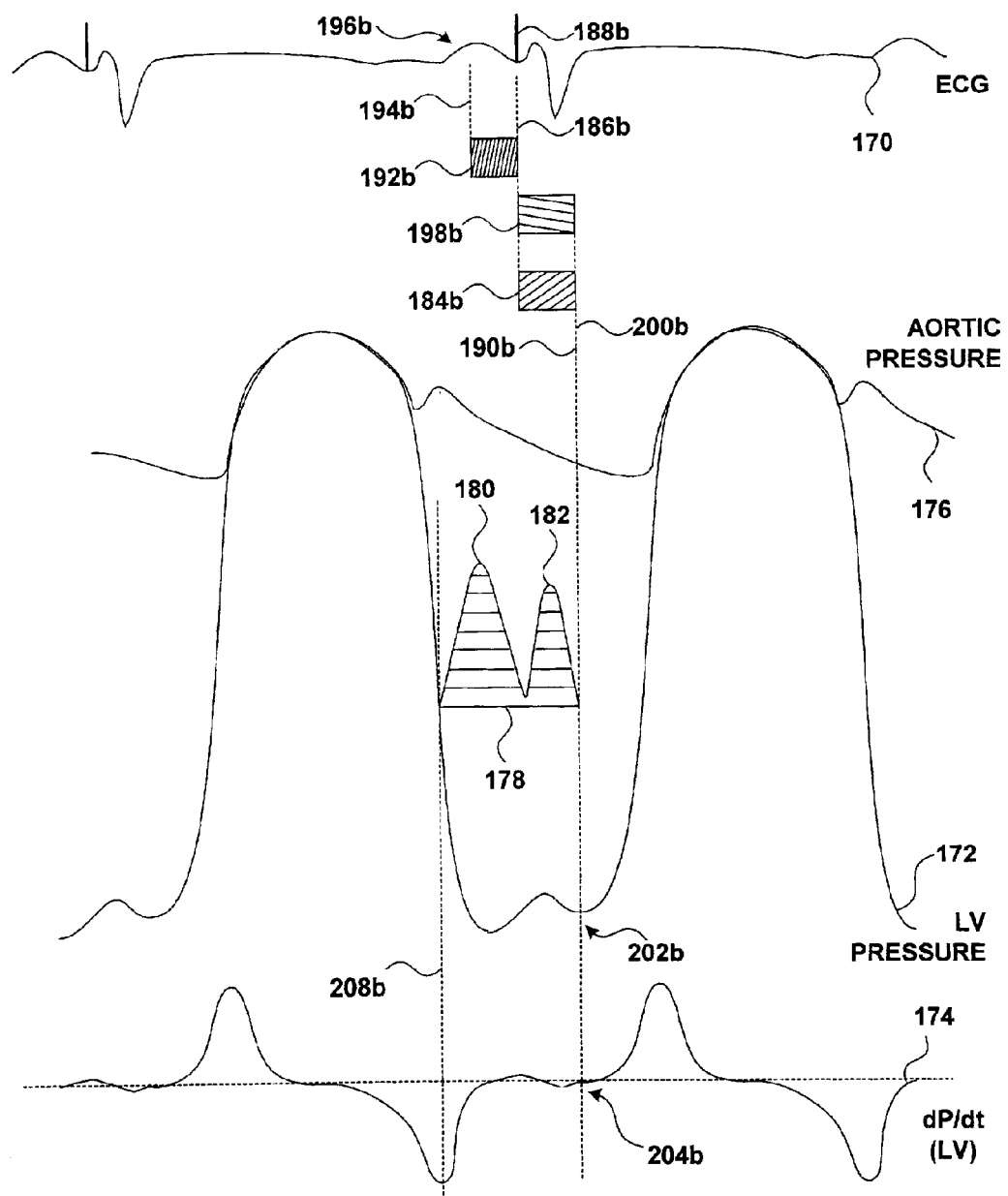
FIG. 9 is a timing diagram illustrating a desirable atrioventricular delay, including an electrocardiogram signal, a corresponding left ventricular pressure signal, a derivative of the left ventricular pressure signal, and a mitral valve flow pattern.

FIG. 9 is a timing diagram showing ECG signal 170, corresponding left ventricular pressure 172, dP/dt 174 and flow pattern 178. In FIG. 9, implanted system 100 has delivered a pacing pulse 188b following a sense of an atrial event, namely P-wave 196b. System 100 applies an adjusted atrioventricular delay 192b that is of shorter duration than baseline atrioventricular delay 192a shown in FIG. 8. In particular, adjusted atrioventricular delay 192b is shorter than baseline atrioventricular delay 192a by DELTA 206 time interval. Accordingly, pacing pulse 188b follows P-wave 196b more closely in FIG. 9 than pacing pulse 188a follows P-wave 196a in FIG. 8.

PACE_CONTRACTION_INTERVAL 198b in FIG. 9 is the same duration as PACE_CONTRACTION_INTERVAL 198a in FIG. 8. Because adjusted atrioventricular delay 192b is shorter than baseline atrioventricular delay 192a, however, isovolumetric contraction commences at an earlier time after atrial event 196b. The isovolumetric contraction is indicated by a sharp upturn 202b in the left ventricular pressure curve 172 and the zero-crossing 204b in dP/dt curve 174. The onset of isovolumetric contraction 200b coincides with the time of mitral valve closure 190b. This is a desirable result, indicating that isovolumetric contraction commences promptly upon completion of ventricular filling, and that heart 8 pumps with good hemodynamic efficiency.

The time of mitral valve closure 190b in FIG. 9 is the same as the time of mitral valve closure 190a in FIG. 8, measured with respect to either the time of mitral valve opening 208a, 208b or atrial event 196a, 196b. In other words, changing the duration of atrioventricular delay 192a, 192b does not affect the duration of ventricular filling. As a result, the duration of the interval 184b in FIG. 9 between the time 186b of administration of pacing pulse 188b and the time of mitral valve closure 190b is longer than PACE_CLOSURE_INTERVAL 184a in FIG. 8.

Unlike PACE_CLOSURE_INTERVAL 184a, interval 184b is not an interval that is measured using techniques such as echo-Doppler. Instead, interval 184b represents a result rather than a measurement. In particular, interval 184b represents the new PACE_CLOSURE_INTERVAL that results from an adjusted atrioventricular delay 192b. Because adjusted atrioventricular delay 192b is shorter than baseline atrioventricular delay 192a, resulting PACE_CLOSURE_INTERVAL 184b is longer than PACE_CLOSURE_INTERVAL 184a.

In other words, by applying a shorter atrioventricular delay 192b, implantable system 100 has caused PACE_CONTRACTION_INTERVAL 198b to be equal to PACE_CLOSURE_INTERVAL 184. In FIG. 9, therefore, DELTA is zero and does not appear in the figure.

Figure 10:
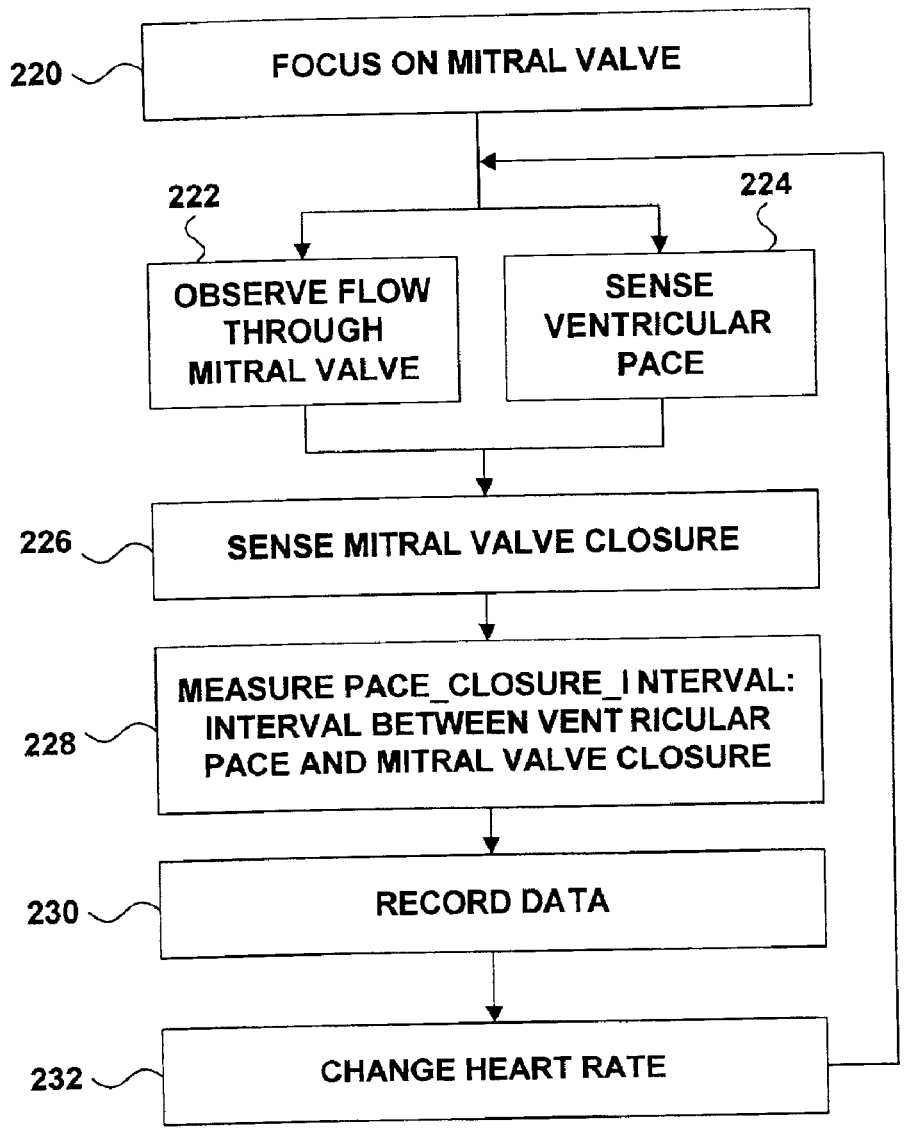
FIG. 10 is a flow diagram illustrating techniques for determining the relationship between heart rate and the interval between a ventricular pace and mitral valve closure.

FIG. 10 illustrates a technique for finding relationships between PACE_CLOSURE_INTERVAL and heart rate. The technique may be performed using a flow pattern sensor such as echo-Doppler. Following location of mitral valve 150 (220), the sensor observes the flow through mitral valve 150 (222), and in the course of the observation, senses a ventricular pacing pulse with an electrocardiograph (224). A baseline atrioventricular delay precedes the ventricular pacing pulses. The sensor observes the time that blood flow through mitral valve 150 stops (226), indicating mitral valve closure. The time between the pacing pulse and mitral valve closure is PACE_CLOSURE_INTERVAL (228) for the current heart rate of the patient. The sensor may compute the heart rate by, for example, measuring the intervals between pacing pulses.

The PACE_CLOSURE_INTERVAL for a particular heart rate is recorded (230). The patient's heart rate may then be changed (232), and the process repeated. In this way, several values of PACE_CLOSURE_INTERVAL for several heart rates may be measured and recorded. The patient's heart rate may be changed (232) by, for example, instructing pacemaker 102 to deliver paces at a different rate, or by causing the patient to exercise.

The values of PACE_CLOSURE_INTERVAL for several heart rates may be organized in any of a number of ways. The data may be compiled in a lookup table for example, or a formula may be derived from the data that defines PACE_CLOSURE_INTERVAL as a function of heart rate.

The techniques shown in FIG. 10 may be embodied as instruction carried by a computer-readable medium such as magnetic or optical tape or disk or read-only memory. The medium may include instructions that cause a processor to carry out the techniques shown in FIG. 10. In some embodiments, such instructions may be downloaded, for example, from a programmer to the implantable device via input/output devices 126, 128.

Figure 11:
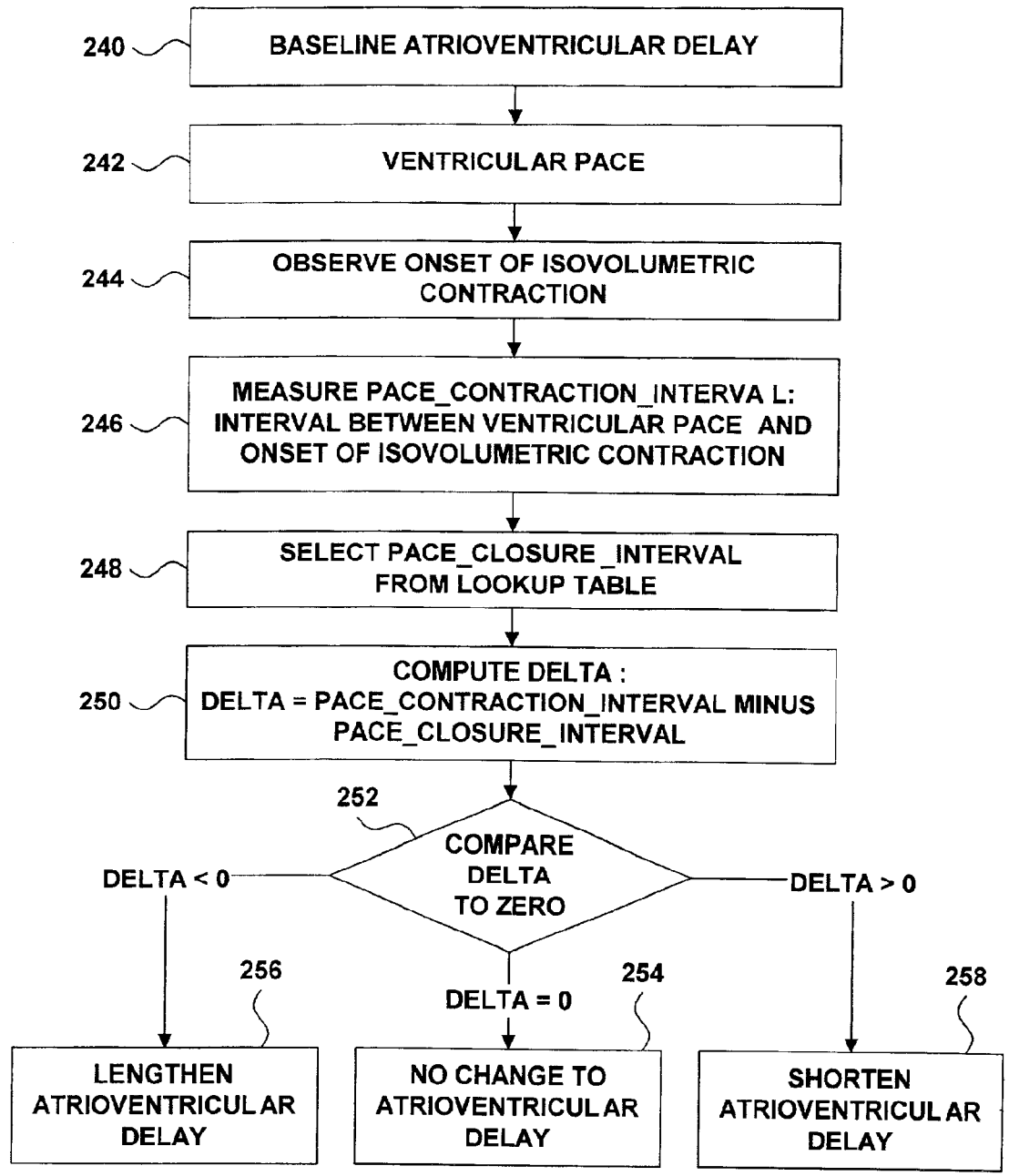
FIG. 11 is a flow diagram illustrating techniques for adjusting the atrioventricular delay as a function of heart rate, electrical measurements and pressure measurements.

FIG. 11 illustrates techniques for adjusting the atrioventricular delay as a function of heart rate, electrical measurements and pressure measurements. At the outset, implantable system 100 paces with a baseline atrioventricular delay (240). The baseline atrioventricular delay is the same baseline atrioventricular delay used when measurements of PACE_CLOSURE_INTERVAL were compiled. Following an atrial event such as an atrial sense or an atrial pace, and following the atrioventricular delay, pacemaker 102 delivers a ventricular pace (242).

Implantable system 100 observes the time of onset of isovolumetric contraction (244) by analysis of pressure data received via pressure sensor 118. In particular, processor 122 may monitor the onset of isovolumetric contraction by observing the upturn in left ventricular pressure curve 172, or by observing the zero crossing that begins the positive upturn of dP/dt curve 174. Processor 122 may measure the time interval between delivery of the ventricular pace (242) and the onset of isovolumetric contraction (244). This interval is PACE_CONTRACTION_INTERVAL (246).

As noted above, implantable system 100 may monitor the heart rate of the patient on a continuous basis. Processor 122 may select a value of PACE_CLOSURE_INTERVAL that corresponds to the heart rate of the patient (248). In one implementation of the invention, values of PACE_CLOSURE_INTERVAL may be stored in a lookup table in memory 124, and processor 122 selects the appropriate value of PACE_CLOSURE_INTERVAL from the lookup table. Processor 122 may select the appropriate value of PACE_CLOSURE_INTERVAL using other techniques as well, such as application of a formula that defines PACE_CLOSURE_INTERVAL as a function of heart rate.

Processor 122, after measuring PACE_CONTRACTION_INTERVAL (246) and selecting PACE_CLOSURE_INTERVAL (248), subtracts one interval from the other to obtain DELTA (250). Processor 122 compares DELTA to zero (252). When DELTA equals zero, then no adjustment to the baseline atrioventricular delay is needed (254), because isovolumetric contraction commences promptly upon completion of active filling.

When DELTA is less than zero, isovolumetric contraction commences before filling is completed. Accordingly, processor 122 applies an adjusted atrioventricular delay that is longer than the baseline atrioventricular delay (256) by the absolute value of DELTA. When DELTA is greater than zero, filling is completed, but isovolumetric contraction does not commence promptly. Accordingly, processor 122 applies an adjusted atrioventricular delay that is shorter than the baseline atrioventricular delay (258) by the absolute value of DELTA.

The invention encompasses variations of this technique. For example, processor 122 may select a value of PACE_CLOSURE_INTERVAL before measuring PACE_CONTRACTION_INTERVAL. Processor 122 may also compute DELTA by subtracting PACE_CONTRACTION_INTERVAL from PACE_CLOSURE_INTERVAL. In that event, the atrioventricular delay should be no greater than zero.

The techniques depicted in FIG. 11 may be repeated. The cardiologist for the patient may, for example, program processor 122 to evaluate the atrioventricular at a set time every day, or in response to activity detected by activity sensor 11 shown in FIG. 3, or in response to changes in heart rate. When the evaluation is made, system 100 may temporarily return to the baseline atrioventricular delay (240) for purposes of applying the techniques.

The techniques shown in FIG. 11 may be embodied as a computer-readable medium such as magnetic or optical tape or disk or read-only memory. The medium may include instructions that cause a processor to carry out the techniques shown in FIG. 11. The processor that carries out the instructions may be processor 122 in FIG. 6.

The invention may be advantageous in many respects. By synchronizing the onset of ventricular isovolumetric contraction with the completion of ventricular filling, the invention promotes hemodynamic performance. In particular, the invention reduces losses to stroke volume and cardiac output that may occur when ventricular isovolumetric contraction with the completion of ventricular filling are unsynchronized. As a result, the hemodynamic performance of the heart may be near optimum. In addition, the invention is adjustable in response to a change in heart rate, so that near-optimum hemodynamic performance may be maintained when the heart rate of the patient changes.

The preceding specific embodiments are illustrative of the practice of the invention. It is to be understood, therefore, that other expedients known to those skilled in the art or disclosed herein may be employed without departing from the invention or the scope of the claims. For example, the present invention is not limited to measurements of PACE_CLOSURE_INTERVAL made by a flow pattern sensor that is outside the body of the patient. It may be possible to implant a sensor that can accurately measure the interval between a ventricular pace and the time of closure of an atrioventricular valve. In such a case, PACE_CLOSURE_INTERVAL may be measured directly at any heart rate, rather than obtained from a lookup table or computed from a formula.

Furthermore, the invention is not limited to intervals measured with respect to a ventricular pace. Intervals may be measured with respect to another cardiac occurrence, but for many patients the ventricular pace represents the best reference point.

The intervals may be measured, for example, with respect to an atrial pace. In that case, PACE_CLOSURE_INTERVAL and PACE_CONTRACTION_INTERVAL are measured with respect to an atrial pace rather than a ventricular pace. In other respects, the techniques described above are the same. In particular, a DELTA is computed and the atrioventricular delay is adjusted by DELTA. By comparison, however, few patients receive both atrial and ventricular pacing, so using an atrial pace as a reference is not available for those patients.

The invention also encompasses intervals measured with respect to an atrial sensed event, such as a P-wave. In that case, PACE_CLOSURE_INTERVAL and PACE_CONTRACTION_INTERVAL may be supplanted by PWAVE_CLOSURE_INTERVAL and PWAVE_CONTRACTION_INTERVAL. In other respects, however, the techniques described above are the same. There are practical difficulties associated with using the P-wave as a sense reference, however. The pacemaker and the flow pattern sensor, for example, may sense the P-wave at different sites and may apply different threshold detection parameters. Consequently, the pacemaker and the flow pattern sensor may not sense the P-wave at the same time. Moreover, when the flow pattern sensor uses an electrocardiograph, the P-wave may be difficult to detect. The ventricular pace, by contrast, represents a "bright line," an unmistakable and easily detectable reference point for both the pacemaker and the flow pattern sensor.

The invention also includes within its scope any of computer-readable media comprising instructions for causing a programmable processor, such as microprocessor, to carry out the techniques described above. Such computer-readable media include, but are not limited to, magnetic and optical storage media, and read-only memory such as erasable programmable read-only memory or flash memory accessible by the processor. The media may be included in a programmer, for example, or in read-only memory accessible by an implanted processor.

These and other embodiments are within the scope of the following claims. In the claims, means-plus-functions clauses are intended to cover the recited structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. An implantable medical device system comprising:
   a pacemaker that paces a ventricle of a heart at an atrioventricular delay following an atrial event;
   a pressure monitor that monitors the onset of isovolumetric contraction of the heart; and
   a processor that:
      selects a first interval representing a time between a first cardiac occurrence and an atrioventricular valve closure, wherein the cardiac occurrence is one of an atrial sense, an atrial pace and a ventricular pace;
      measures a second interval as a function of a time between a second cardiac occurrence and an onset of isovolumetric contraction;
      computes a difference between the first interval and the second interval; and
      adjusts the atrioventricular delay as a function of the computed difference.

2. The system of claim 1, wherein the processor selects the first interval as a function of a measured heart rate.

3. The system of claim 1, wherein the first interval represents a time between a ventricular pace and a mitral valve closure.

4. The system of claim 1, wherein measuring the second interval comprises measuring a pressure in a left ventricle of the heart.

5. The system of claim 1, wherein measuring the second interval comprises detecting a zero crossing in the derivative of the pressure in a left ventricle of the heart.

6. The system of claim 1, further comprising a pressure sensor disposed in the left ventricle of the heart, the pressure sensor coupled to the pressure monitor.

7. The system of claim 6, further comprising a lead having a proximal end and a distal end, wherein the pressure sensor is disposed on the distal end of the lead, and wherein the distal lead penetrates an interventricular septum of the heart.

8. The system of claim 1, further comprising an atrial electrode coupled to the pacemaker, the atrial electrode disposed in an atrium of the heart.

9. The system of claim 1, wherein the atrial event is a sensed atrial activation.

10. The system of claim 1, wherein the atrial event is an atrial pacing pulse.

11. The system of claim 1, further comprising memory that stores a lookup table of values of the first interval as a function of heart rate, and wherein the processor selects a value of the first interval from the lookup table as a function of a measured heart rate.

12. The system of claim 1, further comprising memory that stores a formula that defines the first interval as a function of heart rate, and wherein the processor computes a value of the first interval by applying the formula to a measured heart rate.

13. The system of claim 1, wherein the pacemaker, the pressure monitor and the processor are included in a single implantable device.

14. The system of claim 1, further comprising a ventricular electrode coupled to the pacemaker, the ventricular electrode disposed proximate to a ventricle of the heart.

15. The system of claim 14, wherein the ventricular electrode is disposed in a right ventricle of the heart.

16. The system of claim 1, wherein the processor computes the computed difference by taking the difference between the first interval and the second interval.

17. A method comprising:
 selecting a first interval representing a time between a first cardiac occurrence and an atrioventricular valve closure, wherein the cardiac occurrence is one of an atrial sense, an atrial pace and a ventricular pace;
 measuring a second interval as a function of a time between a second cardiac occurrence and an onset of isovolumetric contraction;
 computing a difference between the first interval and the second interval; and
 adjusting the atrioventricular delay as a function of the computed difference.

18. The method of claim 17, further comprising measuring a heart rate, wherein selecting the value of the first interval comprises selecting the value of the first interval as a function of the measured heart rate.

19. The method of claim 17, wherein the first interval represents a time between a ventricular pace and a mitral valve closure.

20. The method of claim 17, wherein measuring the second interval comprises measuring a pressure in a left ventricle of the heart.

21. The method of claim 17, wherein measuring the second interval comprises detecting a zero crossing in the derivative of the pressure in a left ventricle of the heart.

22. The method of claim 17, wherein selecting a value of first interval comprises selecting a value of first interval from a lookup table as a function of a measured heart rate.

23. The method of claim 17, wherein computing the computed difference comprises taking the difference between the first interval and the second interval.

24. The method of claim 17, wherein computing the computed difference comprises subtracting the first interval from the second interval.

25. The method of claim 24, wherein adjusting an atrioventricular delay comprises shortening the atrioventricular delay when the computed difference is positive.

26. A computer-readable medium comprising instructions that cause a processor to:
 select a first interval representing a time between a first cardiac occurrence and an atrioventricular valve closure, wherein the cardiac occurrence is one of an atrial sense, an atrial pace and a ventricular pace;
 measure a second interval as a function of a time between a second cardiac occurrence and an onset of isovolumetric contraction;
 compute a difference between the first interval and the second interval; and
 adjust the atrioventricular delay as a function of the computed difference.

27. The medium of claim 26, the instructions further causing the processor to measure a heart rate, wherein selecting the value of the first interval comprises selecting the value of the first interval as a function of the measured heart rate.

28. The medium of claim 26, wherein the first interval represents a time between a ventricular pace and a mitral valve closure.

29. The medium of claim 26, wherein measuring the second interval comprises measuring a pressure in a left ventricle of the heart.

30. The medium of claim 26, wherein measuring the second interval comprises detecting a zero crossing in the derivative of the pressure in a left ventricle of the heart.

31. The medium of claim 26, wherein selecting a value of the first interval comprises selecting a value of the first interval from a lookup table as a function of a measured heart rate.

32. The medium of claim 26, wherein computing the computed difference comprises taking the difference between the first interval and the second interval.

33. A method comprising:
 measuring a first time interval between a first ventricular pace and a first atrioventricular valve closure at a first heart rate;
 measuring a second time interval between a second ventricular pace and a second atrioventricular valve closure at a second heart rate;
 recording the first time interval as function of the first heart rate; and
 recording the second time interval as a function of the second heart rate.

34. The method of claim 33, wherein recording the first time interval as function of the first heart rate and recording the second time interval as a function of the second heart rate comprises generating a lookup table that maps the first time interval to the first heart rate and the second time interval to the second heart rate.

35. The method of claim 33, wherein recording the first time interval as function of the first heart rate and recording the second time interval as a function of the second heart rate comprises generating a formula that maps the time intervals to the heart rates.

36. The method of claim 33, wherein the first atrioventricular valve closure and the second atrioventricular valve closure comprise a first mitral valve closure and a second mitral valve closure.

37. The method of claim 33, wherein measuring the first time interval between the first ventricular pace and the first atrioventricular valve closure comprises:
 observing a ventricular pace; and
 measuring a time interval from the ventricular pace to a cessation of blood flow through the first atrioventricular valve.

38. A computer-readable medium comprising instructions that cause a processor to:
  measure a first time interval between a first ventricular pace and a first atrioventricular valve closure at a first heart rate;
  measure a second time interval between a second ventricular pace and a second atrioventricular valve closure at a second heart rate;
  record the first time interval as function of the first heart rate; and
  record the second time interval as a function of the second heart rate.

39. The medium of claim 38, wherein recording the first time interval as function of the first heart rate and recording the second time interval as a function of the second heart rate comprises generating a lookup table that maps the first time interval to the first heart rate and the second time interval to the second heart rate.

40. The medium of claim 38, wherein recording the first time interval as function of the first heart rate and recording the second time interval as a function of the second heart rate comprises generating a formula that maps the time intervals to the heart rates.

41. The medium of claim 38, wherein the first atrioventricular valve closure and the second atrioventricular valve closure comprise a first mitral valve closure and a seconds mitral valve closure.

42. The medium of claim 38, wherein the instructions cause the processor to measure the first time interval between the first ventricular pace and the first atrioventricular valve closure by causing the processor to:
  observe a ventricular pace; and
  measure a time interval from the ventricular pace to a cessation of blood flow through the first atrioventricular valve.

43. An implantable medical device system, comprising:
  a pacemaker that paces a ventricle of a heart at an atrioventricular delay following an atrial event;
  a pressure monitor that monitors the onset of isovolumetric contraction of the heart; and
  a processor that:
    selects a value of a first interval representing a time between a ventricular pace and an atrioventricular valve closure;
    measures a second interval as a function of a time between a second ventricular pace and an onset of isovolumetric contraction;
    computes a difference between the first interval and the second interval; and
    adjusts the atrioventricular delay as a function of the difference.

44. The system of claim 43, wherein the processor selects the first interval as a function of a measured heart rate.

45. The system of claim 43, wherein measuring the second interval comprises measuring a pressure in a left ventricle of the heart.

46. The system of claim 43, further comprising a pressure sensor disposed in the left ventricle of the heart, the pressure sensor coupled to the pressure monitor.

47. The system of claim 43, wherein the pacemaker, the pressure monitor and the processor are included in a single implantable device.

48. A method comprising:
  selecting a value of a first interval representing a time between a first ventricular pace and an atrioventricular valve closure;
  measuring a second interval as a function of a time between a second ventricular pace and an onset of isovolumetric contraction;
  computing a difference between the first interval and the second interval; and
  adjusting an atrioventricular delay as a function of the difference.

49. The method of claim 48, further comprising measuring a heart rate, wherein selecting the value of the first interval comprises selecting the value of the first interval as a function of the measured heart rate.

50. The method of claim 48, wherein measuring the second interval comprises measuring a pressure in a left ventricle of the heart.

51. A computer-readable medium comprising instructions that cause a processor to:
  select a value of a first interval representing a time between a first ventricular pace and an atrioventricular valve closure;
  measure a second interval as a function of a time between a second ventricular pace and an onset of isovolumetric contraction;
  compute a difference between the first interval and the second interval; and
  adjust an atrioventricular delay as a function of the difference.

52. The medium of claim 51, the instructions further causing the processor to measure a heart rate, wherein selecting the value of the first interval comprises selecting the value of the first interval as a function of the measured heart rate.

53. The medium of claim 51, wherein measuring the second interval comprises measuring a pressure in a left ventricle of the heart.

54. An implantable medical device system comprising:
  means for pacing a ventricle of a heart at an atrioventricular delay following an atrial event;
  means for monitoring the onset of isovolumetric contraction of the heart; and
  means for selecting a value of a first interval representing a time between a first cardiac occurrence and an atrioventricular valve closure, wherein the cardiac occurrence is one of an atrial sense, an atrial pace and a ventricular pace;
  means for measuring a second interval as a function of a time between a second cardiac occurrence and an onset of isovolumetric contraction;
  means for computing a difference between the first interval and the second interval; and
  means for adjusting the atrioventricular delay as a function of the difference.

55. The system of claim 54, further comprising means for selecting the first interval as a function of a measured heart rate.

56. The system of claim 54, further comprising means for measuring a pressure in a left ventricle of the heart.

57. The system of claim 54, further comprising means for sensing atrial activation.

58. The system of claim 54, further comprising means for pacing an atrium.

59. The system of claim 54, further comprising means for pacing a ventricle.

60. The system of claim 54, further comprising means for storing a lookup table of values of the first interval as a function of heart rate.

61. An implantable medical device comprising:

a pulse generator that applies paces to a ventricle of a heart;

a controller that controls the pulse generator to deliver each of the paces at an atrioventricular delay following an atrial event, wherein the atrioventricular delay is a function of a difference between a first value representing a time between a first ventricular pace and an atrioventricular valve closure, and a second value as a function of a time between a second ventricular pace and an onset of isovolumetric contraction.

62. The device of claim 61, further comprising a pressure monitor that monitors the onset of isovolumetric contraction.

63. The device of claim 62, further comprising a pressure sensor coupled to the pressure monitor.

64. The device of claim 63, wherein the pressure sensor is disposed in the left ventricle of the heart.

65. The device of claim 61, wherein the first value is a function of a measured heart rate.

66. The device of claim 61, wherein the atrial event is a sensed atrial activation.

67. A method comprising:

measuring a first interval representing a time between a first cardiac occurrence and an atrioventricular valve closure, wherein the cardiac occurrence is one of an atrial sense, an atrial pace and a ventricular pace;

measuring a second interval as a function of a time between a second cardiac occurrence and an onset of isovolumetric contraction;

adjusting an atrioventricular delay to cause the first interval to equal the second interval.

68. The method of claim 67, further comprising:

measuring a primary first interval at a first heart rate; and measuring a secondary first interval at a second heart rate.

69. The method of claim 67, wherein measuring the first interval comprises measuring a flow through the atrioventricular valve.

70. The method of claim 67, further comprising setting a baseline atrioventricular delay, and wherein adjusting the atrioventricular delay comprises setting an adjusted atrioventricular delay that is of a different duration than the baseline atrioventricular delay.

71. The method of claim 67, further comprising programming an implantable medical device to pace according to the adjusted atrioventricular delay.

\* \* \* \* \*